United States Patent
Gong et al.

(10) Patent No.: US 10,184,904 B1
(45) Date of Patent: Jan. 22, 2019

(54) CORE HOLDER FOR MICRON CT OBSERVATION AND EXPERIMENTAL METHOD THEREOF

(71) Applicant: PetroChina Company Limited, Beijing (CN)

(72) Inventors: Yanjie Gong, Beijing (CN); Mengjun Zhao, Beijing (CN); Qingong Zhuo, Beijing (CN); Xuesong Lu, Beijing (CN); Lin Jiang, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 0 days.

(21) Appl. No.: 15/961,231

(22) Filed: Apr. 24, 2018

(30) Foreign Application Priority Data

Nov. 17, 2017 (CN) .......................... 2017 1 1142575

(51) Int. Cl.
*G01N 23/20* (2018.01)
*G01N 23/20025* (2018.01)
(Continued)

(52) U.S. Cl.
CPC ... *G01N 23/20025* (2013.01); *G01N 15/0806* (2013.01); *G01N 23/046* (2013.01); *G01N 33/241* (2013.01)

(58) Field of Classification Search
CPC ......... G01N 23/20025; G01N 15/0806; G01N 23/046
See application file for complete search history.

(56) References Cited

U.S. PATENT DOCUMENTS

| 4,669,299 A | 6/1987 | Closmann |
| 4,856,341 A | 8/1989 | Vinegar et al. |

(Continued)

FOREIGN PATENT DOCUMENTS

| CN | 103969166 A | 8/2014 |
| CN | 104316548 A | 1/2015 |

(Continued)

OTHER PUBLICATIONS

Gao et al., "Application of CT Scanning Image Technique to Study of Oil Saturation Distribution in Core Displacement Test", Xinjiagn Petroleum Geology, vol. 30, No. 2, Apr. 2009, pp. 269-271.
(Continued)

*Primary Examiner* — Hugh H Maupin
(74) *Attorney, Agent, or Firm* — Hoffman Warnick LLC

(57) ABSTRACT

The present disclosure discloses a core holder for a micron CT observation and an experimental method thereof. The core holder for a micron CT observation comprises: a carbon fiber pipe and a base; the base comprises a fluid injection channel therein; the carbon fiber pipe is provided with a core mounting cavity and a carbon fiber plunger therein; the carbon fiber pipe is a tubular structure with one end closed and the other end open; the carbon fiber plunger can fix the core between the closed end of the carbon fiber pipe and the carbon fiber plunger; the other end of the carbon fiber pipe is in a detachable sealed connection with an outlet of the fluid injection channel of the base. The core holder for a micron CT observation reduces the distance between the core and the micron CT radiation source, and improves the resolution.

10 Claims, 9 Drawing Sheets

(51) Int. Cl.
*G01N 15/08* (2006.01)
*G01N 23/046* (2018.01)
*G01N 33/24* (2006.01)

(56) References Cited

U.S. PATENT DOCUMENTS

| | | | |
|---|---|---|---|
| 5,065,421 A * | 11/1991 | Morineau | G01N 15/0806 |
| | | | 378/208 |
| 2010/0126266 A1 | 5/2010 | Coenen | |
| 2012/0148431 A1* | 6/2012 | Gabriel | F16J 15/32 |
| | | | 417/559 |
| 2016/0077023 A1 | 3/2016 | Alshehri et al. | |
| 2016/0216218 A1 | 7/2016 | Grader | |
| 2018/0148988 A1* | 5/2018 | Dusterhoft | E21B 49/06 |

FOREIGN PATENT DOCUMENTS

| | | |
|---|---|---|
| CN | 106596596 A | 4/2017 |
| CN | 106706684 A | 5/2017 |

OTHER PUBLICATIONS

Combined Search and Examination Report for UK Patent Application No. 1805542.6, dated Sep. 27, 2018, 5 pages.

\* cited by examiner

CORE HOLDER FOR MICRON CT OBSERVATION AND EXPERIMENTAL METHOD THEREOF

FIELD OF THE DISCLOSURE

The present disclosure relates to the field of experimental facilities, and particularly, to a core holder for a micron CT observation, and an experimental method of a micron CT observation of cores.

BACKGROUND OF THE DISCLOSURE

In the core analysis physical simulation experiments, CT has played an increasingly important role. Regarding the tight sandstone, the main reservoir system is composed of micro and Nano scale pores, the micron CT resolution can reach 0.7 μm, and the micron CT can effectively realize the three-dimensional distribution reconstruction of the reservoir space of the tight sandstone, therefore, a good effect can be achieved by representing the microscopic pore characteristics of the tight sandstone with the micron CT. The underground rocks are all in certain temperature and pressure systems, and in order to represent the core characteristics under the real geological status with the micron CT, the core must be placed in a core holder capable of bearing a certain temperature and pressure, and then a fluid injection is performed for heating and pressurization. But the core holder usually has a certain thickness, and the fluid injection certainly requires the space of the core holder to be increased. The distance between the core and the micron CT radiation source increases as the size of the core hold grows, while the pores of the tight sandstone are all of micro and Nano scales, so it is necessary to reduce the distance between the core and the micron CT radiation source to increase the resolution. Currently at home and abroad, there is still no tight sandstone high-temperature and high-pressure (fluid pressure) core holder that can be effectively applied to the micron CT observation.

SUMMARY OF THE DISCLOSURE

In order to solve the problem that the existed core holders are not suitable for the micron CT observation, the present disclosure provides a core holder for a micron CT observation and an experimental method thereof. The core holder for the micron CT observation reduces the distance between the core and the micron CT radiation source, and improves the resolution.

The present disclosure solves its technical problem using the following technical solutions: a core holder for a micron CT observation, comprising a carbon fiber pipe and a base; the base comprises a fluid injection channel therein; the carbon fiber pipe is provided with a core mounting cavity and a carbon fiber plunger therein; the carbon fiber pipe is a tubular structure with one end closed and the other end open; the carbon fiber plunger can fix the core between the closed end of the carbon fiber pipe and the carbon fiber plunger; the other end of the carbon fiber pipe is in a detachable sealed connection with an outlet of the fluid injection channel of the base.

The base is a plate-like structure, the core is able to be in a clearance fitting with the carbon fiber pipe, the carbon fiber plunger is in a clearance fitting with the carbon fiber pipe, and two ends of the carbon fiber plunger abut against the core and the base along an axial direction of the carbon fiber pipe, respectively.

The base is a plate-like structure, a length of the carbon fiber pipe is 120 mm to 160 mm, an inner diameter of the carbon fiber pipe is 5 mm, a wall thickness of the carbon fiber pipe is 5 mm, and a length of the core is 5 mm to 10 mm.

The base is a plate-like structure, the other end of the carbon fiber pipe is provided with an external thread, the outlet of the fluid injection channel is provided with an internal thread, and the other end of the carbon fiber pipe is in a threaded connection with the outlet of the fluid injection channel of the base.

The base is a plate-like structure; the outlet of the fluid injection channel is located at a middle portion of the base, and an inlet of the fluid injection channel is located at an edge of the base; an axial through hole is provided in the carbon fiber plunger, and a peripheral surface of the carbon fiber plunger is provided with a plurality of strip-shaped outer grooves opened along an axial direction of the carbon fiber plunger and sequentially arranged in a peripheral direction of the carbon fiber plunger.

The base is a bow, the outlet of the fluid injection channel is at a center of a circle where the bow is located, and a central angle corresponding to an arc of the bow is 240° to 330°. The fluid injection channel comprises an axial segment and a radial segment; the axial segment of the fluid injection channel is provided along an axial direction of the bow, and the radial segment of the fluid injection channel is provided along a diameter direction of the bow; the axial segment and the radial segment are communicated with each other; and the radial segment of the fluid injection channel is parallel with a bottom edge of the bow.

A surface of the base corresponding to the carbon fiber pipe is a front surface, and the axial segment passes through the front surface and a back surface of the base; the axial segment comprises a first segment and a second segment connected in sequence; an inner diameter of the first segment is larger than an inner diameter of the second segment, and an inner diameter of the carbon fiber pipe is larger than the inner diameter of the second segment; an annular transition surface is provided between the first segment and the second segment; the first segment is corresponding to the front surface of the base, and the second segment is corresponding to the back surface of the base; one end of the first segment is the outlet of the fluid injection channel, and one end of the second segment is fixed with an exhaust valve which is located on the back surface of the base; an annular groove is provided at an outer edge of the annular transition surface which is provided with radial grooves communicating the annular groove with the second segment; the radial segment is communicated with the first segment, and two ends of the carbon fiber plunger can abut against the core and the annular transition surface, respectively.

A surface of the base corresponding to the outlet of the fluid injection channel is a front surface; three blind holes are provided on the front surface of the base, and uniformly distributed along a peripheral direction of the base; two of the three blind holes are equidistant from the bottom edge of the bow; a projection of the blind hole on the front surface of the base is a racetrack, a lengthwise direction of which is arranged along a diameter direction of the bow; along the lengthwise direction thereof, the racetrack is composed of a first semi-circular surface, a rectangular surface and a second semi-circular surface connected in sequence; the first semi-circular surface is inclined relative to the front surface of the base, the first semi-circular surface and the second semi-circular surface mirror each other, and the rectangular surface is parallel to the front surface of the base.

The core holder for a micron CT observation further comprises a pipe joint, wherein an external thread is provided at an outlet of the pipe joint, which outlet is in a threaded sealed connection with the inlet of the fluid injection channel, and an inlet of the pipe joint can be connected to a fluid injection line.

An experimental method of a micron CT observation of cores, employing the above core holder for a micron CT observation, comprising:

step 1: directing a closed end of a carbon fiber pipe downwards and an open end thereof upwards; placing a core and a carbon fiber plunger into the carbon fiber pipe in sequence, so that the open end of the carbon fiber pipe is in a sealed connection with an outlet of a fluid injection channel of a base; and connecting the base to a fluid injection line;

step 2: rotating the carbon fiber pipe to a horizontal state;

step 3: putting the core holder into a micron CT for a scanning.

The present disclosure has the following advantageous effects:

1. As compared with the traditional holder for a micron CT, which needs to wrap the core with a rubber case, the present disclosure directly places the core into the carbon fiber pipe, and only a tiny gap is reserved between the carbon fiber pipe and the core; by pressurizing fluid with the injected fluid, the wall thickness of the core holder is greatly decreased, the distance between the core and the micron CT irradiation source is reduced, and the resolution is improved.

2. The carbon fiber pipe is directly engaged with the base, which is beneficial to the holder pressure maintaining and sealing.

BRIEF DESCRIPTION OF THE DRAWINGS

The drawings constituting a part of the present disclosure are employed to provide a further understanding of the present disclosure. The schematic embodiments of the present disclosure and the descriptions thereof are used to explain the present disclosure, rather than improperly limiting the present disclosure.

1: core; 2: carbon fiber pipe; 3: carbon fiber plunger; 4: pipe joint; 5: base; 6: sealing ring; 7: fluid injection line; 8: exhaust valve; 31: axial through hole; 32: strip-shaped outer groove; 33: radial inner groove; 51: fluid injection channel; 52: arc; 53: bottom edge; 54: blind hole; 55: first semi-circular surface; 56: rectangular surface; 57: second semi-circular surface; 58: axial segment; 59: radial segment; 510: first segment; 511: second segment; 512: annular transition surface; 513: annular groove; 514: radial groove; 515: exhaust valve.

DETAILED DESCRIPTION OF THE PREFERRED EMBODIMENTS

It should be noted that, when there is no conflict, the embodiments in the present disclosure and the features in the embodiments may be combined with each other. The present disclosure will be described below in details with reference to the drawings and in conjunction with the embodiments.

Embodiment 1

Figure 1:
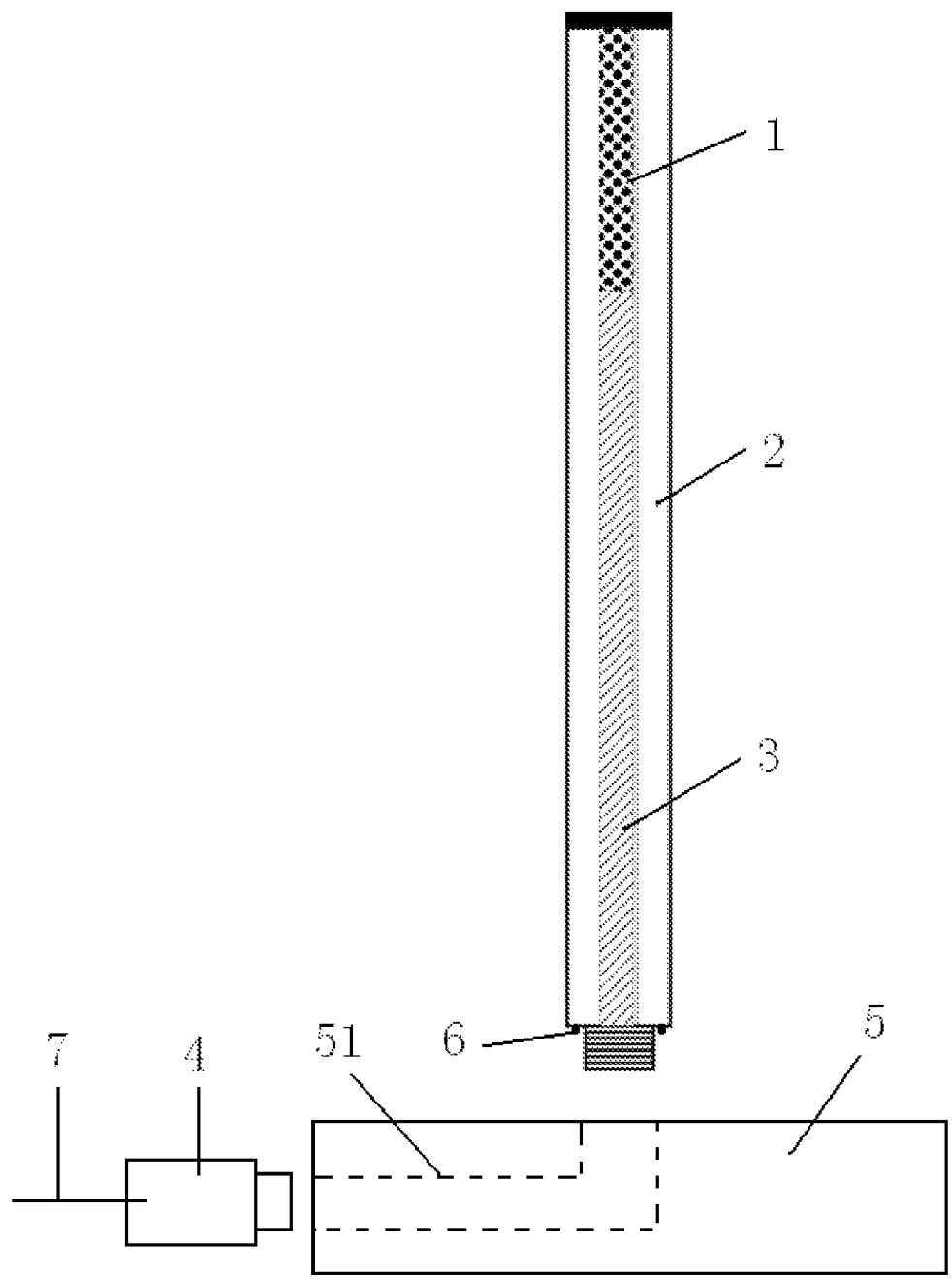
FIG. 1 is an exploded schematic view of a core holder for a micron CT observation according to the present disclosure.

A core holder for a micron CT observation comprises a carbon fiber pipe 2 and a base 5; the base 5 comprises a fluid injection channel 51 therein; the carbon fiber pipe 2 is provided with a core mounting cavity and a carbon fiber plunger 3 therein; the carbon fiber pipe 2 is a tubular structure with one end closed and the other end open; the carbon fiber plunger 3 can fix the core 1 between the closed end of the carbon fiber pipe 2 and the carbon fiber plunger 3; the other end of the carbon fiber pipe 2 is in a detachable sealed connection with an outlet of the fluid injection channel 51 of the base 5, as shown in FIG. 1.

In this embodiment, the carbon fiber pipe 2 should be able to bear a high-temperature and high-pressure environment required for the experiment. The core 1 can be in a clearance fitting with the carbon fiber pipe 2, the carbon fiber plunger 3 is in a clearance fitting with the carbon fiber pipe 2, and the core 1 and the carbon fiber plunger 3 can be manually mounted into the core mounting cavity in the carbon fiber pipe 2 in sequence. After the carbon fiber pipe 2 and the base 5 are assembled together, two ends of the carbon fiber plunger 3 abut against the core 1 and the base 5 along an axial direction of the carbon fiber pipe 2, respectively, i.e., the function of the carbon fiber plunger 3 is to locate the core 1.

Preferably, a length of the carbon fiber pipe 2 is 120 mm to 160 mm, an inner diameter of the carbon fiber pipe 2 is 5 mm, a wall thickness of the carbon fiber pipe 2 is 5 mm, and a length of the core 1 is 5 mm to 10 mm. The other end of the carbon fiber pipe 2 is provided with an external thread, the outlet of the fluid injection channel 51 is provided with an internal thread, and the other end of the carbon fiber pipe 2 is in a threaded connection with the outlet of the fluid injection channel 51 of the base 5. In order to improve the sealing effect, the other end of the carbon fiber pipe 2 is further provided with a sealing ring 6 (Φ6×1.9). The carbon fiber pipe 2 can be commercially available. The material of the carbon fiber pipe 2 is PEEK with a carbon fiber content of 30%, i.e., in the carbon fiber pipe 2, a mass fraction of the carbon fiber is 30% and a mass fraction of the PEEK is 70%. The materials of the carbon fiber pipe 2 and the carbon fiber plunger 3 may be the same, and the manufacturing method is manual cutting and grinding. The main performance of carbon fiber pipe 2 is the pressure resistance which is improved as the thickness increases while the resolution is reduced. The carbon fiber pipe 2 bears a pressure more than 50 MPa, which is higher than the currently bearable pressure of 30 MPa of the carbon fiber holder at home and abroad.

In the prior art, the heating and pressurization of the core holder is mainly realized by a fluid injection system, which generally includes an external high-temperature and high-pressure line, a high-temperature and high-pressure valve, and the like. The presence of these external devices is a big problem for the scanning process of the core holder. The main reason is that since the core and the fluid in the holder need to maintain a certain pressure, certain lines and valves should be kept outside the holder to ensure that the holder maintains the internal temperature and pressure. However, the core holder needs to be rotated by 360° for a scanning in the CT device, and the presence of these external devices greatly increases the distance between the core and the CT device source (radiation source), while the increase of the distance results in a reduction of the resolution index according to the principle of X-ray imaging. Therefore, how to design a fluid injection system embedded into an interior or a bottom of the holder is the difficulty faced by the core holder.

Figure 2:
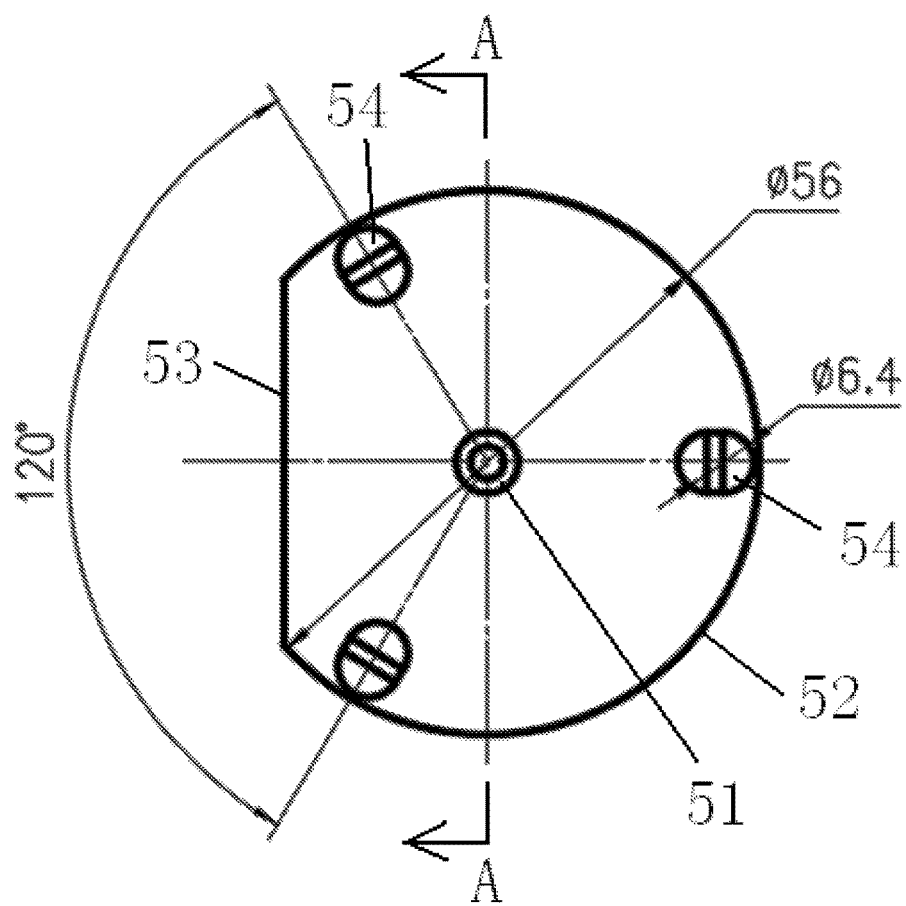
FIG. 2 is a front view of a base.
Figure 3:
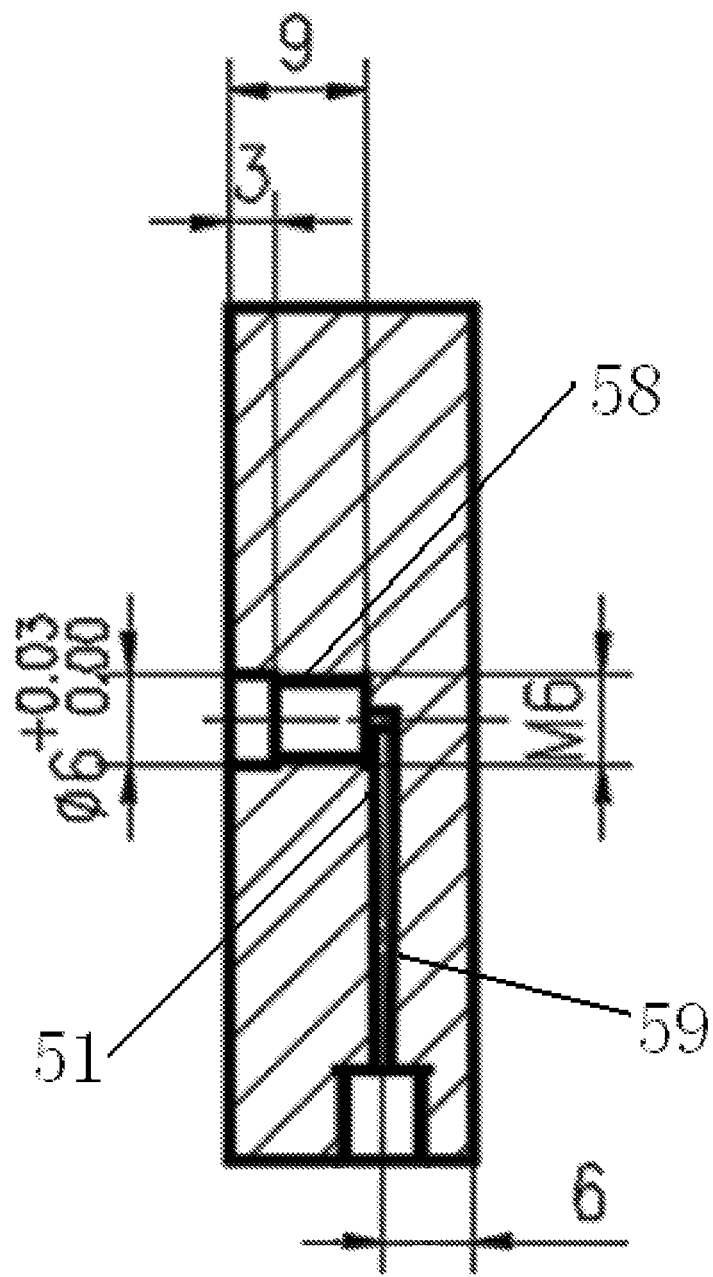
FIG. 3 is a cross-sectional view taken along direction A-A in FIG. 2.

In order to solve the difficulty, the present disclosure makes a special design of the base 5. The base 5 is a plate-like structure and made of stainless steel, and capable of withstanding a pressure of 70 MPa; the fluid injection channel 51 is completely provided in the base 5, wherein the outlet of the fluid injection channel 51 is located at a middle portion of the base 5, and an inlet of the fluid injection channel 51 is located at an edge of the base 5, as shown in FIGS. 2 and 3. This design greatly simplifies the injection structure, and the periphery of the core no longer contains any injection line, thereby reducing the distance between the core and the CT device source (radiation source), and further increasing the resolution.

In this embodiment, the base 5 is shaped as a bow, as shown in FIG. 2, comprising an arc 52 and a bottom edge 53, two ends of the bottom edge 53 being connected to corresponding two ends of the arc 52. The outlet of the fluid injection channel 51 is at a center of a circle where the bow is located, the inlet of the fluid injection channel 51 is on the arc 52 of the bow, and a central angle corresponding to the arc 52 of the bow is 240° to 330°, as shown in FIGS. 2 and 3.

In this embodiment, the fluid injection channel 51 comprises an axial segment 58 and a radial segment 59. The axial segment 58 of the fluid injection channel 51 is provided along an axial direction of the bow; for example, a center line of the axial segment 58 coincides with a center line of the circle where the bow is located; the radial segment 59 of the fluid injection channel 51 is provided along a diameter direction of the bow; for example, a center line of the radial segment 59 of the fluid injection channel 51 coincides with a radius of the circle where the bow is located, while parallel with the bottom edge 53 of the bow; and the axial segment 58 and the radial segment 59 are communicated with each other, as shown in FIG. 3.

In this embodiment, a surface of the base 5 corresponding to the outlet of the fluid injection channel 51 is a front surface, i.e., a surface of the base 5 facing an outer side of a principal plane of FIG. 2 is the front surface, and a face of the base 5 facing a left side of a principal plane of FIG. 3 is the front surface. Three blind holes 54 are provided on the front surface of the base 5, and uniformly distributed along a peripheral direction of the base 5, wherein two of the three blind holes 54 are equidistant from the bottom edge 53 of the bow. The three blind holes 54 are matched the three protrusions on the CT base to facilitate the holding and fixing by the core holder.

Figure 4:
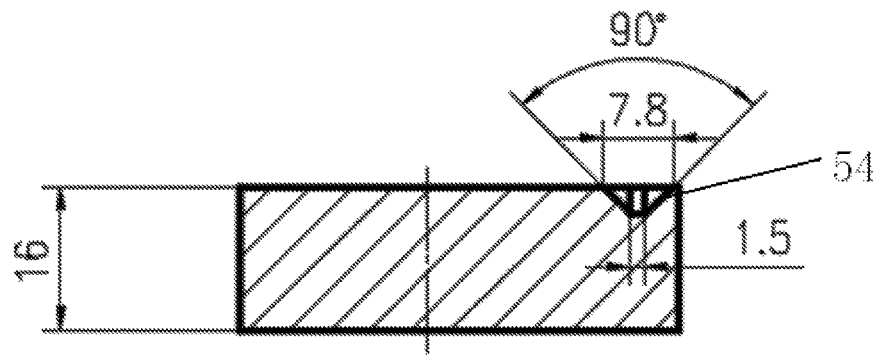
FIG. 4 is a cross-sectional view of a blind hole portion.
Figure 5:
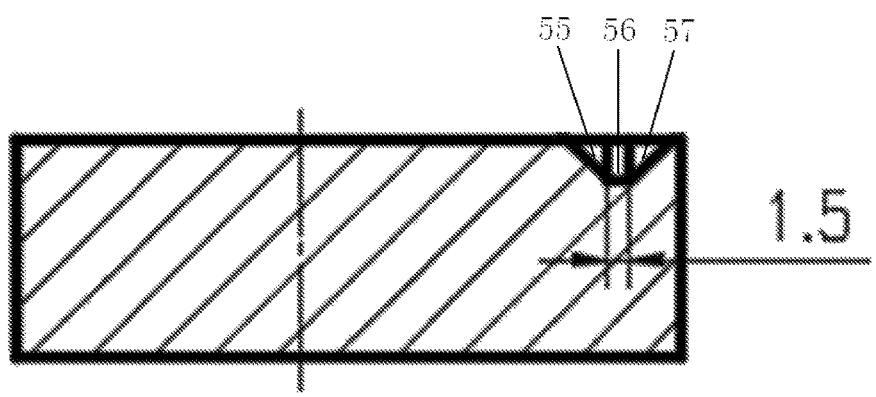
FIG. 5 is an enlarged schematic view of a blind hole portion.

Specifically, a projection of the blind hole 54 on the front surface of the base 5 is shaped as a racetrack (as shown in FIG. 2), a lengthwise direction of which is arranged along a diameter direction of the bow. Along the lengthwise direction thereof, the racetrack is composed of a first semi-circular surface 55, a rectangular surface 56 and a second semi-circular surface 57 which are connected in sequence. The first semi-circular surface 55 is inclined relative to the front surface of the base 5, the first semi-circular surface 55 and the second semi-circular surface 57 mirror each other, and the rectangular surface 56 is parallel to the front surface of the base 5, as shown in FIGS. 4 and 5.

After the core 1 and the carbon fiber plunger 3 are placed into the carbon fiber pipe 2 and the carbon fiber pipe 2 is connected to the base 5, when high-temperature and high-pressure liquid is injected into the core mounting cavity of the carbon fiber pipe 2, air in the core mounting cavity cannot be discharged. In order to discharge air in the core mounting cavity, the present disclosure further designs the carbon fiber plunger 3 and the base 5.

In this embodiment, an axial through hole 31 is provided in the carbon fiber plunger 3, and a peripheral surface of the carbon fiber plunger 3 is provided with a plurality of strip-shaped outer grooves 32 opened along an axial direction of the carbon fiber plunger 3 and sequentially arranged in a peripheral direction of the carbon fiber plunger 3. The strip-shaped outer grooves 32 and the axial through hole 31 allow the high-temperature and high-pressure liquid to enter the core 1, and also discharge the gas around the core 1.

Figure 10:
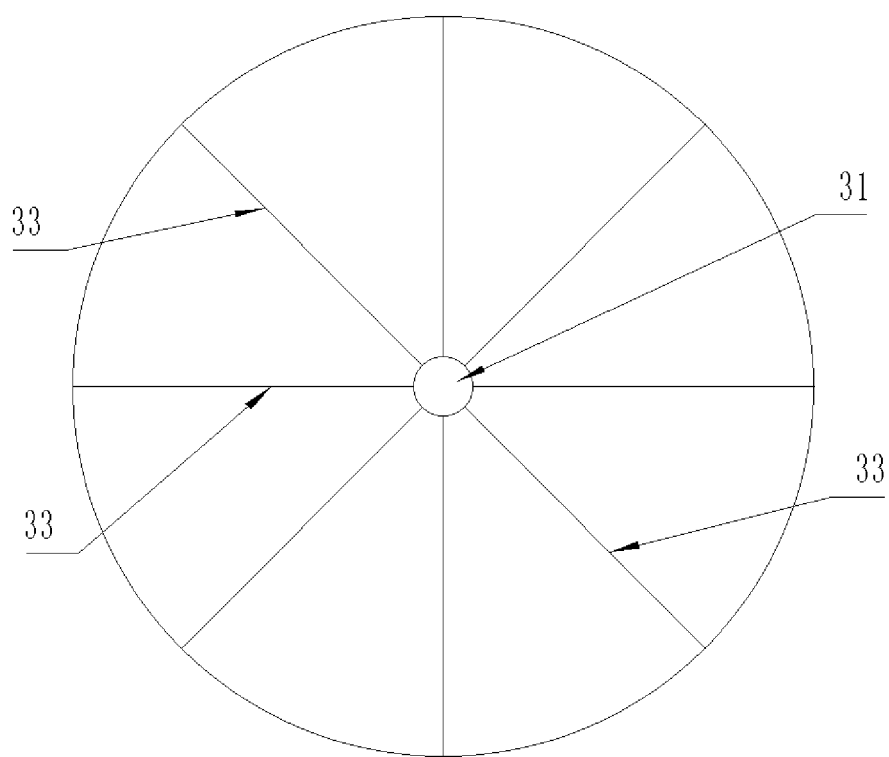
FIG. 10 is another schematic end view of a carbon fiber plunger.

Alternatively, the structure of the carbon fiber plunger 3 may be as shown in FIG. 10. The carbon fiber plunger 3 is provided therein with an axial through hole 31, a cross section of either end of the carbon fiber plunger 3 is provided with a plurality of radial inner grooves 33 arranged in a radial direction of the carbon fiber plunger 3, and two ends of each radial inner groove 33 are communicated with an outer peripheral surface of the carbon fiber plunger 3 of the axial through hole 31. Alternatively, the carbon fiber plunger 3 may also comprise an axial through hole 31, a plurality of strip-shaped outer grooves 32, and a plurality of radial inner grooves 33 at the same time.

Figure 6:
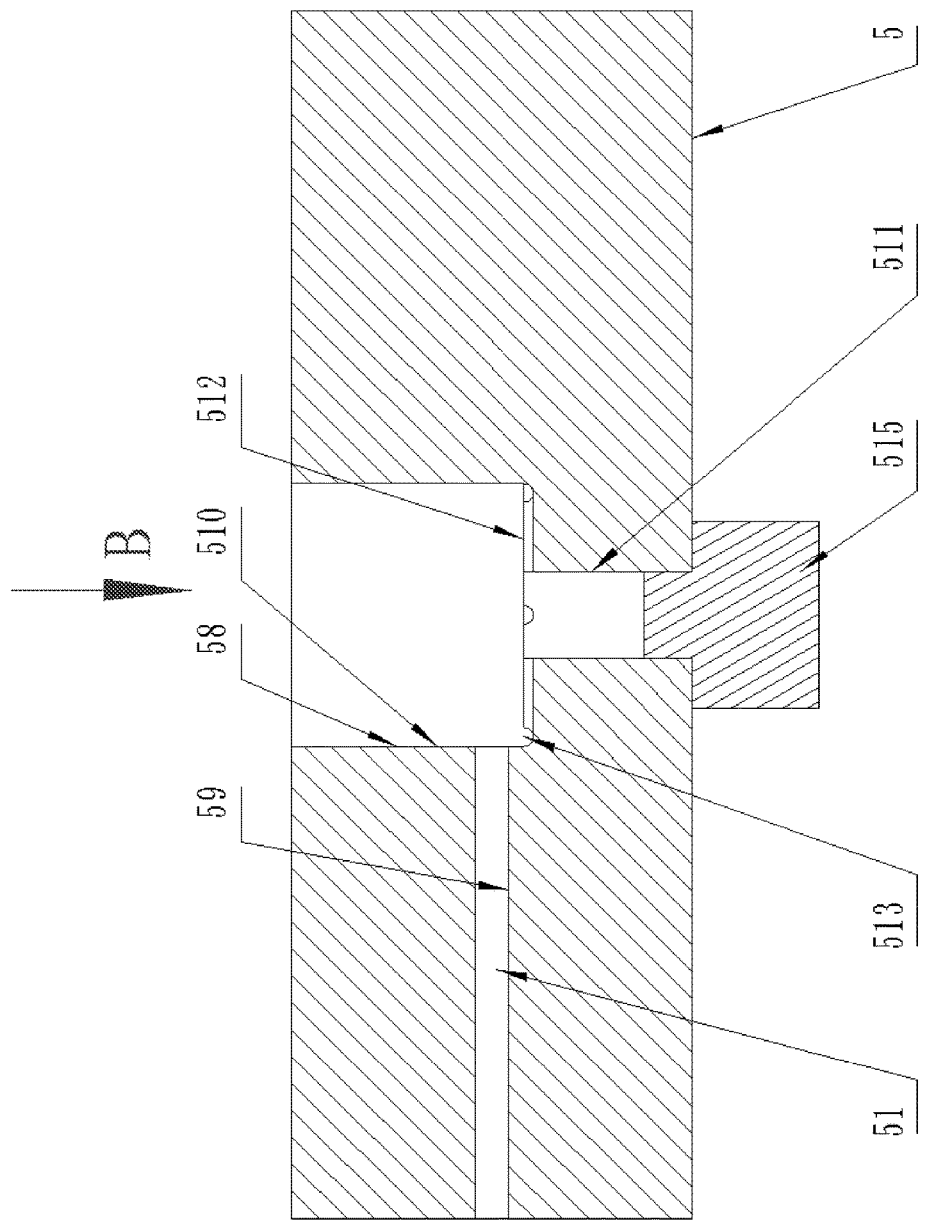
FIG. 6 is another cross-sectional view of a base.
Figure 7:
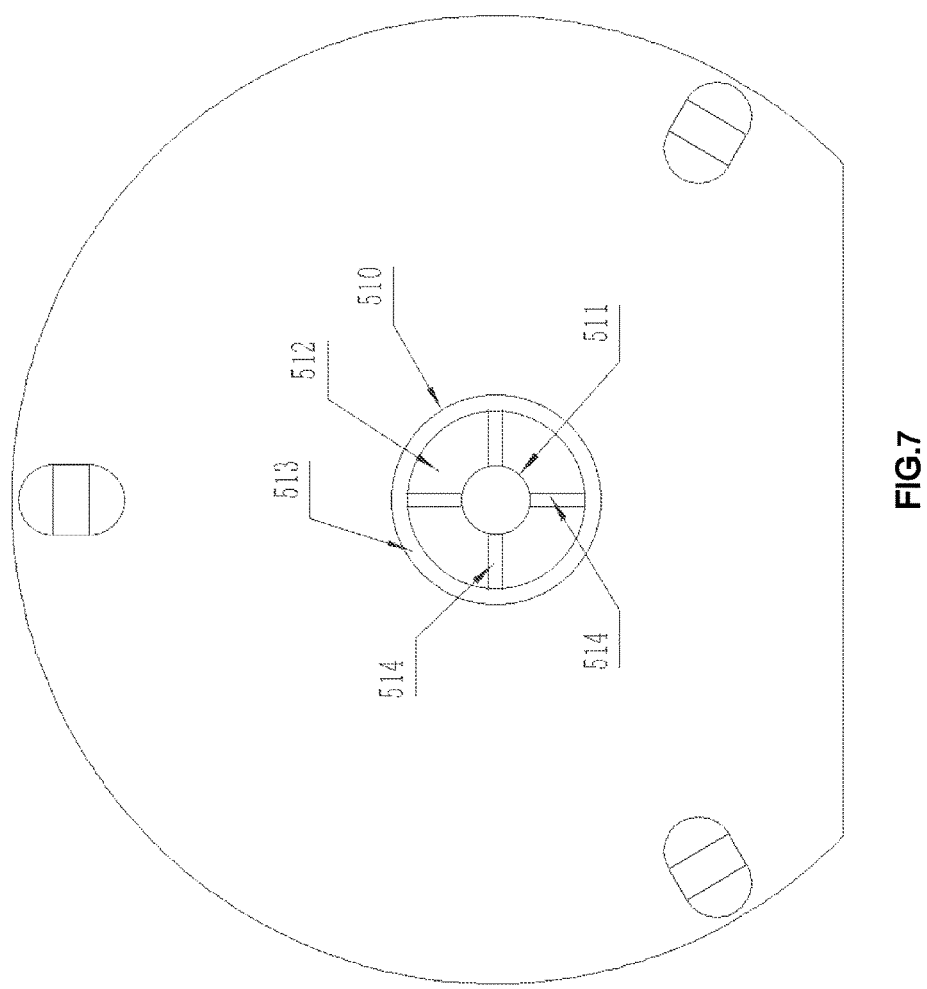
FIG. 7 is a schematic view along direction B in FIG. 6.
Figure 8:
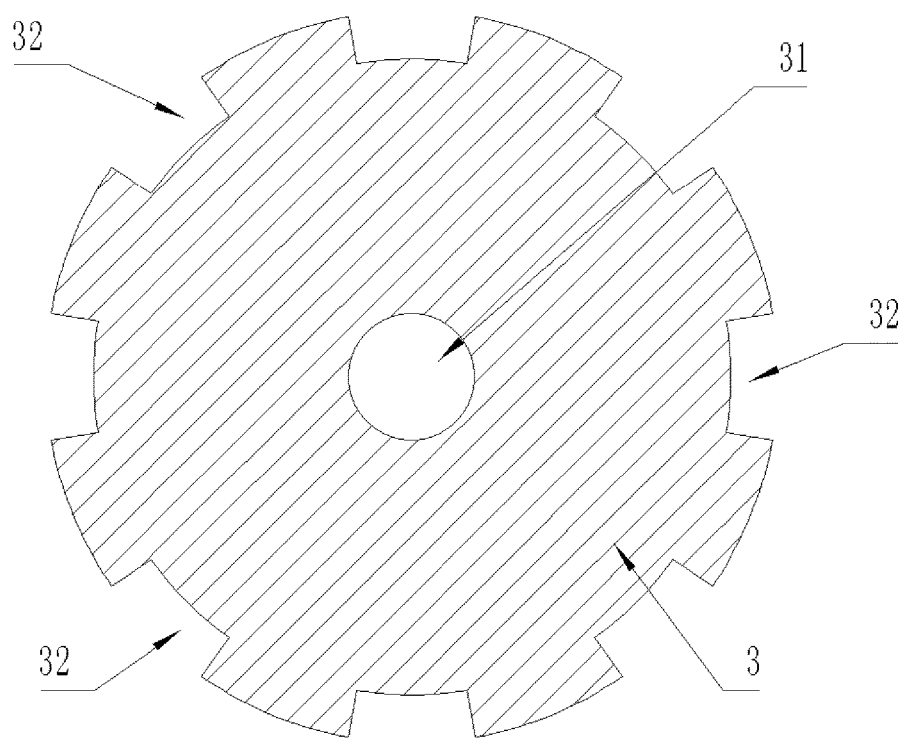
FIG. 8 is a schematic view along direction B in FIG. 6.
Figure 9:
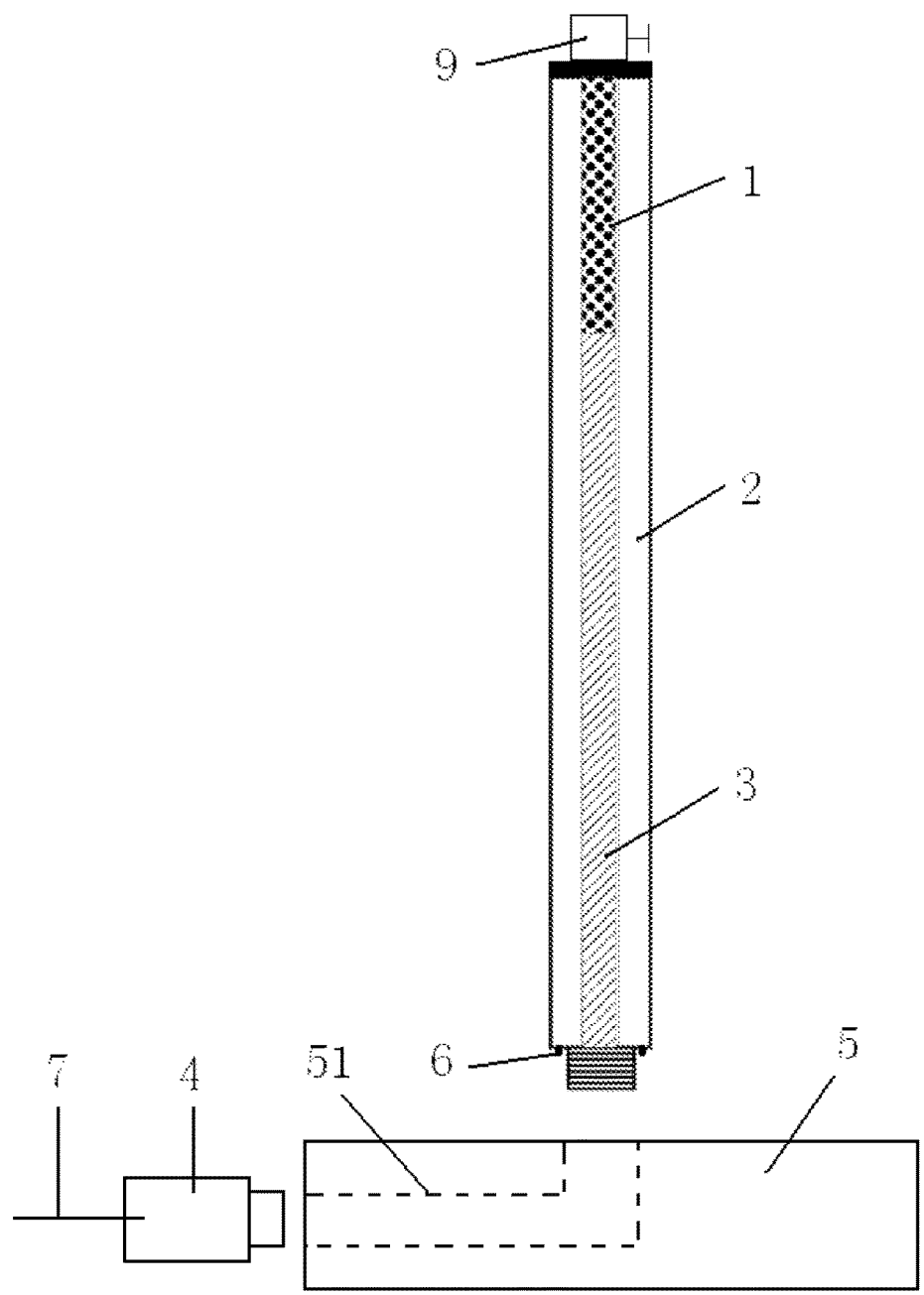
FIG. 9 is another exploded schematic view of a core holder for a micron CT observation.

In this embodiment, a surface of the base 5 corresponding to the carbon fiber pipe 2 is the front surface, i.e., in FIG. 1, an upper surface of the base 5 is the front surface, and a lower surface of the base 5 is a back surface. The axial segment 58 passes through the front surface and the back surface of the base 5. The axial segment 58 comprises a first segment 510 and a second segment 511 connected in sequence. An inner diameter of the first segment 510 is larger than an inner diameter of the second segment 511, an inner diameter of the carbon fiber pipe 2 is larger than the inner diameter of the second segment 511, and an outer diameter of the carbon fiber plunger 3 is larger than the inner diameter of the second segment 511. An annular transition surface 512 is provided between the first segment 510 and the second segment 511. The first segment 510 is corresponding to the front surface of the base 5, i.e., one end of the first segment 510 is connected to the front surface of the base 5. The second segment 511 is corresponding to the back surface of the base 5, i.e., one end of the second segment 511 is connected to the back surface of the base 5. One end of the first segment 510 is the outlet of the fluid injection channel 51, and one end of the second segment 511 is fixed with an exhaust valve 515 which is located on the back surface of the base 5. An annular groove 513 is provided at an outer edge of the annular transition surface 512 which is provided with radial grooves 514 communicating the annular groove 513 with the second segment 511. The radial segment 59 is communicated with the first segment 510, as shown in FIGS. 6 and 7. After the core 1 and the carbon fiber plunger 3 are placed into the carbon fiber pipe 2 and the carbon fiber pipe 2 is connected to the base 5, two ends of the carbon fiber plunger 3 can abut against the core 1 and the annular transition surface 512, respectively.

Thus, when high-temperature and high-pressure liquid is injected into the carbon fiber pipe 2, the closed end of the carbon fiber pipe 2 is directed downwards and the open end of the carbon fiber pipe 2 is directed upwards; the exhaust valve 515 is in an open state; and after entering the core mounting cavity of the carbon fiber pipe 2, the liquid moves downwards to push the gas upwards; the gas is discharged from the exhaust valve 515 after passing through the strip-shaped outer groove 32, the annular groove 513, the radial groove 514, and the second segment 511 in sequence. The gas may also be discharged from the exhaust valve 515 after passing through the axial through hole 31 and the second segment 511 in sequence.

In this embodiment, the core holder for the micron CT observation further comprises a pipe joint 4, wherein an external thread is provided at an outlet of the pipe joint 4, a ⅛ pipe thread is provided at an inlet of the fluid injection channel 51, the outlet of the pipe joint 4 is in a threaded sealed connection with the inlet of the fluid injection channel 51, and the inlet of the pipe joint 4 can be connected to the fluid injection line.

Next, an experimental method of a micron CT observation of cores will be introduced, which employs the above core holder for the micron CT observation, comprising:

step 1: directing a closed end of a carbon fiber pipe 2 downwards and an open end thereof upwards; placing a core 1 and a carbon fiber plunger 3 into the carbon fiber pipe 2 in sequence, so that the open end of the carbon fiber pipe 2 is in a sealed connection with an outlet of a fluid injection channel 51 of a base 5; and connecting the base 5 to a fluid injection line 7;

step 2: rotating the carbon fiber pipe 2 to a horizontal state in which a center line of the carbon fiber pipe 2 is parallel to a horizontal plane;

step 3: putting the core holder into micron CT for a scanning.

Specifically, the structure of the base 5 is shown in FIGS. 6 and 7, and the experimental method of the micron CT observation of cores comprises the following steps:

In step 1, the core 1 and the carbon fiber plunger 3 of appropriate sizes are prepared as needed, so that the closed end of carbon fiber pipe 2 is directed downwards and the open end of the carbon fiber pipe 2 is directed upwards (i.e., the carbon fiber pipe 2 in FIG. 1 is rotated by) 180°; the core 1 and the carbon fiber plunger 3 are placed into the carbon fiber pipe 2, as shown in FIG. 1, the carbon fiber pipe 2 is in a sealed connection with the outlet of the fluid injection channel 51 in the base 5, and the inlet of the fluid injection channel 51 in the base 5 is in a sealed connection with the fluid injection line 7 through the pipe joint 4;

the exhaust valve 515 is kept in an open state, high-temperature and high-pressure liquid is injected into the carbon fiber pipe 2 through the fluid injection line 7 until liquid is discharged from the exhaust valve 515, and then the exhaust valve 515 is closed;

next, the carbon fiber pipe 2 is tapped or shaken, the exhaust valve 515 is opened again until liquid is discharged from the exhaust valve 515, and the exhaust valve 515 is closed again; this process (tapping or shaking the carbon fiber pipe 2, opening the exhaust valve 515 again until liquid is discharged from the exhaust valve 515, and then closing the exhaust valve 515 again) can be repeated several times.

In step 2, the carbon fiber pipe 2 is rotated into a horizontal state, and fluid is injected into the carbon fiber pipe 2 through a pump body, so as to achieve the desired experimental pressure and temperature.

In the present disclosure, the unit of size is mm.

Embodiment 2

When high-temperature and high-pressure liquid is injected into the core mounting cavity of the carbon fiber pipe 2, air in the core mounting cavity may not be discharged. In order to facilitate the discharge of the air in the core mounting cavity, in this embodiment, the closed end of the carbon fiber pipe 2 is provided with an exhaust valve 8 through which the air in the core mounting cavity can be discharged.

The rest of the technical features in this embodiment are the same as those in Embodiment 1, which are not described in details herein in order to save space.

Those described as above are merely specific embodiments of the present disclosure and cannot limit the implementation scope of the invention. Thus, replacements of the equivalent components, or equivalent changes and modifications made according to the patent protection scope of the present disclosure should still fall within the coverage of this patent. Moreover, in the present disclosure, different technical features can be freely combined with each other, any technical feature and any technical solution can be freely combined with each other, and different technical solutions can also be freely combined with each other.

The invention claimed is:

1. A core holder for a micron CT observation, comprising a carbon fiber pipe and a base; the base comprises a fluid injection channel therein; the carbon fiber pipe is provided with a core mounting cavity and a carbon fiber plunger therein; the carbon fiber pipe is a tubular structure with one end closed and the other end open; the carbon fiber plunger can fix the core between the closed end of the carbon fiber pipe and the carbon fiber plunger; the other end of the carbon fiber pipe is in a detachable sealed connection with an outlet of the fluid injection channel of the base.

2. The core holder for a micron CT observation according to claim 1, wherein the base is a plate-like structure, the core is in a clearance fitting with the carbon fiber pipe, the carbon fiber plunger is in a clearance fitting with the carbon fiber pipe, and two ends of the carbon fiber plunger abut against the core and the base along an axial direction of the carbon fiber pipe, respectively.

3. The core holder for a micron CT observation according to claim 1, wherein the base is a plate-like structure, a length of the carbon fiber pipe is 120 mm to 160 mm, an inner diameter of the carbon fiber pipe is 5 mm, a wall thickness of the carbon fiber pipe is 5 mm, and a length of the core is 5 mm to 10 mm.

4. The core holder for a micron CT observation according to claim 1, wherein the base is a plate-like structure, the other end of the carbon fiber pipe is provided with an external thread, the outlet of the fluid injection channel is provided with an internal thread, and the other end of the carbon fiber pipe is in a threaded connection with the outlet of the fluid injection channel of the base.

5. The core holder for a micron CT observation according to claim 1, wherein the base is a plate-like structure; the outlet of the fluid injection channel is located at a middle portion of the base, and an inlet of the fluid injection channel is located at an edge of the base; an axial through hole is provided in the carbon fiber plunger, and a peripheral surface of the carbon fiber plunger is provided with a plurality of strip-shaped outer grooves opened along an axial direction of the carbon fiber plunger and sequentially arranged in a peripheral direction of the carbon fiber plunger.

6. The core holder for a micron CT observation according to claim 5, wherein the base is a bow, the outlet of the fluid injection channel is at a center of a circle where the bow is located, and a central angle corresponding to an arc of the bow is 240° to 330°.

7. The core holder for a micron CT observation according to claim 6, wherein the fluid injection channel comprises an axial segment and a radial segment; the axial segment of the fluid injection channel is provided along an axial direction of the bow, and the radial segment of the fluid injection channel is provided along a diameter direction of the bow; the axial segment and the radial segment are communicated with each other; and the radial segment of the fluid injection channel is parallel with a bottom edge of the bow.

8. The core holder for a micron CT observation according to claim 7, wherein a surface of the base corresponding to the carbon fiber pipe is a front surface, and the axial segment passes through the front surface and a back surface of the base; the axial segment comprises a first segment and a second segment connected in sequence; an inner diameter of the first segment is larger than an inner diameter of the second segment, and an inner diameter of the carbon fiber pipe is larger than the inner diameter of the second segment; an annular transition surface is provided between the first segment and the second segment; the first segment is corresponding to the front surface of the base, and the second segment is corresponding to the back surface of the base; one end of the first segment is the outlet of the fluid injection channel, and one end of the second segment is fixed with an exhaust valve which is located on the back surface of the base; an annular groove is provided at an outer edge of the annular transition surface which is provided with radial grooves communicating the annular groove with the second segment; the radial segment is communicated with the first segment, and two ends of the carbon fiber plunger can abut against the core and the annular transition surface, respectively.

9. The core holder for a micron CT observation according to claim 8, wherein three blind holes are provided on the front surface of the base, and uniformly distributed along a peripheral direction of the base; two of the three blind holes are equidistant from the bottom edge of the bow; a projection of the blind hole on the front surface of the base is a racetrack, a lengthwise direction of which is arranged along a diameter direction of the bow; along the lengthwise direction thereof, the racetrack is composed of a first semi-circular surface, a rectangular surface and a second semi-circular surface connected in sequence; the first semi-circular surface is inclined relative to the front surface of the base, the first semi-circular surface and the second semi-circular surface mirror each other, and the rectangular surface is parallel to the front surface of the base.

10. An experimental method of a micron CT observation of cores, employing the core holder for a micron CT observation according to claim 1, comprising:
step 1: directing a closed end of a carbon fiber pipe downwards and an open end thereof upwards; placing a core and a carbon fiber plunger into the carbon fiber pipe in sequence, so that the open end of the carbon fiber pipe is in a sealed connection with an outlet of a fluid injection channel of a base; and connecting the base to a fluid injection line;
step 2: rotating the carbon fiber pipe to a horizontal state;
step 3: putting the core holder into micron CT for a scanning.

\* \* \* \* \*